(12) United States Patent
Zhou et al.

(10) Patent No.: US 7,163,514 B2
(45) Date of Patent: *Jan. 16, 2007

(54) SPECIMEN COLLECTION AND APPLICATION APPARATUS

(75) Inventors: David F. Zhou, San Diego, CA (US); Nai Shu (Sue) Wang, San Diego, CA (US); Claudia J. R. Shen, San Diego, CA (US); Angela J. Q. Shen, San Diego, CA (US)

(73) Assignee: Alfa Scientific Designs, Inc., Poway, CA (US)

( * ) Notice: Subject to any disclaimer, the term of this patent is extended or adjusted under 35 U.S.C. 154(b) by 201 days.

This patent is subject to a terminal disclaimer.

(21) Appl. No.: 10/913,899

(22) Filed: Aug. 5, 2004

(65) Prior Publication Data

US 2005/0036910 A1    Feb. 17, 2005

Related U.S. Application Data

(62) Division of application No. 10/205,712, filed on Jul. 25, 2002, now Pat. No. 6,780,160.

(51) Int. Cl.
*A61B 10/00* (2006.01)
(52) U.S. Cl. ...................................... 600/562
(58) Field of Classification Search ............... 600/562, 600/570, 572; 206/204, 523, 589; 422/58, 422/56, 150, 61; 435/287.6, 309.1; 215/332; 220/295
See application file for complete search history.

(56) References Cited

U.S. PATENT DOCUMENTS

| 3,904,060 | A | | 9/1975 | McPhee |
| 5,078,968 | A | * | 1/1992 | Nason ......................... 422/58 |
| 5,160,021 | A | * | 11/1992 | Sibley et al. ................ 206/204 |
| 6,780,160 | B1 | * | 8/2004 | Zhou et al. ................. 600/562 |

FOREIGN PATENT DOCUMENTS

EP    0638803 A1 *  2/1995

* cited by examiner

*Primary Examiner*—Max Hindenburg
*Assistant Examiner*—Brian Szmal
(74) *Attorney, Agent, or Firm*—Charmasson, Buchaca & Leach, LLP

(57) ABSTRACT

A device for quantitively collecting, preserving and mailing a specimen of fecal or other biological matter for later analysis comprises a tubular vessel defining a chamber closed at one end by a plug and restricted at the opposite end by a narrow aperture. A stopper for closing the open end of the vessel extends into a stick having indentations capable of retaining some of the biological matter. The stick intimately engages the aperture so that the amount of matter introduced into the chamber is limited to what is carried in the indentations. The shank of the stick seals the aperture once the stopper has been screwed into place. The plug mounts a breakable hollow nib and is installed after introduction into the chamber of a metered volume of preserving solution. A cover caps the plug and nib to provide additional sealing of that end of the vessel.

12 Claims, 1 Drawing Sheet

SPECIMEN COLLECTION AND APPLICATION APPARATUS

Prior Application

This is a divisional of U.S. Patent application Ser. No. 10/205,712 filed Jul. 25,2002, now U.S. Pat. No. 6,780,160.

FIELD OF THE INVENTION

This invention relates to methods and devices practiced and used in the collection, preservation, transportation and analysis of biological tissues and bodies, and more specifically to instruments used for collecting specimens of fecal matter or other similar biological material.

BACKGROUND OF THE INVENTION

Several devices and methods have been used in the past to collect, preserve and transport and dispense biomedical specimens including fecal samples for later analysis by a laboratory or for clinical studies. The most common has been a smear paper pad, upon which, in the case of fecal samples, three consecutive specimens are smeared, covered then sent for analysis. One of the most common problems associated with this device and method is dehydration. Even under rehydrating condition, a fecal occult blood test of dry samples on paper pads will give false positive or negative results. A false positive result may trigger a relatively expensive colonoscopic or barium enema examination that will probably or eventually eliminate the false diagnosis. In the case of a false negative result, an early stage colorectal cancer may be missed, and if then metastosis occurs, the cancer may become incurable.

Another fecal sample collection device of the prior art comprises a simple cylindrical tube with a cap having a breakable tip and a plastic stick connected to the inside of the screw cap. The tube contains a certain amount of extraction buffer. The stick is inserted into fresh feces several times then put back into the tube and the cap is tightly secured to seal the tube. The main advantage of this procedure is that the extraction buffer keeps the specimen wet and a preserving reagent mixed therewith may slow down the degradation of the biological molecule or its markers. While this method constitutes a substantial improvement over the smear paper devices of the past, unintended breakdown of the tip on top of the cap has occurred during manipulation of mailing of the specimen resulting in leakage and possible contamination. Moreover, specimens have a tendency to include excessive amounts of fecal material for the amount of preservative or reagent contained in the tube resulting in false positive analysis. Another improved device of the prior art is disclosed in U.S. Pat. No. 6,063,038 Diamond et al. In this case, a filtering membrane is provided between the body of the shipping vessel which holds the specimen and a preserving/reagent solution and the hollowed inside of the stick itself which can be accessed through a self-sealing membrane to extract a part of the liquid containing only the amount of specimen that passed through the filtering membrane. This improved device still suffers from a high risk of spillage of the preservative/reagent and a lack of quantitative mixing of the sample and preserving/reagent fluid.

The instant invention results from some attempt to provide a practical solution to the problems and disadvantages of the aforesaid devices of the prior art.

SUMMARY OF THE INVENTION

The principal and secondary objects of this invention are to provide a convenient, safe and inexpesive to manufacture device and method for collection by a patient or unskilled person of fresh fecal or other biological specimens in a quantitatively metered manner and for the preservation and leakproof shipping of the specimen through the mail to a laboratory for further analysis while avoiding degradation of the specimen through dehydration or imbalance combination of specimen and preserving agents.

These and other valuable objects are achieved by providing a simple tubular vessel closed at one end by a breakable hollow nib or other releasable sealing device that is engaged at the opposite end by a cap or stopper from which a stick axially projects into the vessel. At the distal end of the tip, a sample-holding portion has at least one radial or axial cavity and preferably indentations in the form of a spiral or helicoidal groove. As the stopper and stick are progressively inserted into the vessel by a screwing movement, the sample-holding portion passes through an aperture defining a narrow channel in the center of a septum in the median section of the vessel. The cross-section of the non-grooved part of the sample-holding portion closely match the cross-sectional profile of the aperture so that any access specimen matter which is not contained within an indentation, whether a cavity or groove, is conveniently wiped out and prevented from passing into the most distal chamber of the vessel that contains a preserving fluid. The shank of the stick right behind the sample-holding portion seals the specimen-holding chamber so that the amount of specimen and preserving fluid are quantitatively balanced and remain so until part or all of the fluid is extracted for analysis after breaking of the sealing nib. A cover, shaped and dimensioned to safely cap the breakable nib can be tightly screwed upon the closed end of the vessel to protect the nib during manipulation and shipping of the device. The specimen-holding chamber is thus doubly sealed at opposite ends to ensure against leakage both before and after specimen collection. A padded shipping container made from inexpensive disposable plastic provides a third seal and enhanced protection.

DESCRIPTION OF THE PREFERRED EMBODIMENT OF THE INVENTION

Figure 1:
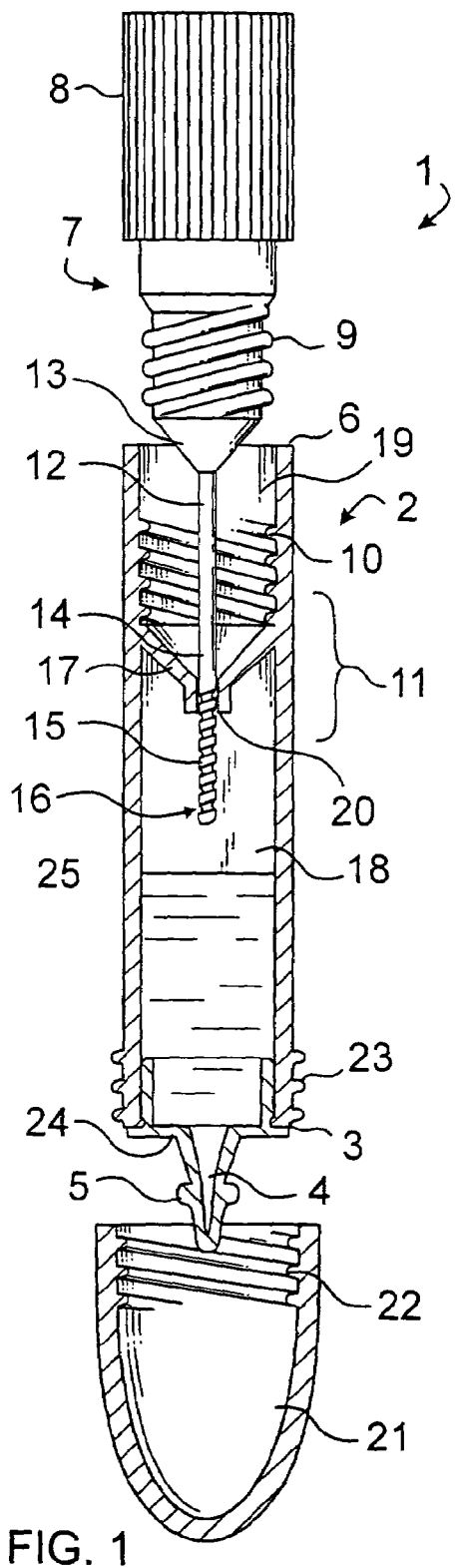
FIG. 1 is a cross-sectional side view of a biological specimen-collecting device according to the invention; and, FIG. 2 is a partial cross-sectional side view of an alternate embodiment of a biological specimen-collecting device carried within a padded mailing container according to the invention.

Referring now to the drawing, there is shown a device 1 specially adapted to collect a specimen of fecal or other biological matter, store and preserve it while it is mailed to a laboratory for analysis. The device comprises a tubular, preferably cylindrical, vessel 2 having a first end 3 closed and defining an access port 4 which is releasably sealed by a hollow nib 5 that can be easily broken to open the access port and allow convenient dispensing. The opposite, normally open, end 6 of the vessel is engaged by a stopper 7 comprising a knob 8 and a threaded plunger 9. Screw threads 10 matingly cooperating with the threaded plunger are provided along the inside wall of the vessel from the second end 6 down to a median portion 11 of the vessel. A stick 12 projects axially from the stopper, more specifically, from the conical distal end 13 of the plunger into the vessel. The stick comprises a shank 14 and a sample-holding distal portion 15. The sample-holding portion consists an oblong cylindrical member into which indentations 16 in the form of an helicoidal groove have been cut. The radius of the distal portion is substantially the same as the radius of the cylindrical shank 14.

A conical transversal septum 17 in the median portion 11 of the vessel divides the vessel into a first chamber 18 sealed by the closed end 3 and a second chamber 19 accessible through the second end 6. An aperture or passageway 20 in the middle of the septum is axially lined up with the stick 12 and has a cross-sectional geometry substantially symmetrical with that of the stick, that is a radius substantially equal to the radius of the shank 14 and sample-holding portion 15. The cooperatively conically shaped distal end 13 of the plunger and septum 17 allow for enahnced resiliency, thereby providing a positive seal over a larger range of plunger positions.

When the knob 8 of the stopper is turned clockwise, the sample-holding portion 15 of the stick progressively translates from the second chamber 19 into the first chamber 18 through the passageway constituted by the aperture 20 until such time as a distal part of the shank 14 engages and seals the aperture as shown in dotted line on the drawing.

A cover 21 shaped and dimensioned to cap the closed first end 3 and end-breakable nib 5 has a threaded inner wall section 22 that cooperates with a correspondingly threaded area 23 on the outer wall of the vessel to secure the cover and thus, protect the breakable nib 5.

The end section 24 that mounts the breakable nib 5 at the first end 3 of the vessel is not molded integrally with the wall of the vessel, but constitutes a separate plug which is installed only after the first chamber 18 has been filled with the preserving fluid 25. The end section 24 is preferably permanently bonded to the vessel with an adhesive. It should be noted that this bonding of the end section and the cover 21 that further occludes both the access port 4 controlled by the breakable nib and the one sealed by the end section plug 24, combined with the double seal provided by the shank 14 of the stick closing the aperture 20 and the stopper 7 closing the second end 6 of the vessel assures against any leakage of the preserving fluid during shipment, before and after collection of the specimen.

The device may be used as follows. At the factory, with plunger 9 fully or partially screwed into the second end of the vessel and the aperture 20 sealed, a measured volume of preserving liquid 25 is introduced into the first chamber through the first end 3 which is then sealed by the installation and bonding of the end section 24. The volume is measured to provide the desired concentration of specimen that will eventually be found in suspension in the liquid. The device is marked about the first end 3, such as on the cover 21, with a legend such as "For Laboratory Use" or "Lab End". The knob 8 or upper area of the vessel is marked with another legend such as "Open Here", or "Patient End". The device is then packaged and distributed for use.

The collection of the specimen by the patient or an assisting individual goes as follows. Holding the stopper 7 by the knob and after unscrewing it and separating it from the vessel, the user plunges the sample-holding portion 15 of the stick into a volume of matter to be analyzed. The stick is then inserted back into the vessel and the stopper is screwed down until the sample-holding portion passes completely through the aperture 20 of the septum. During this procedure, the walls of the aperture coming into intimate contact with the non-threaded part of the sample-holding portion and shank, wipe out any excess material which is not held within the helicoidal groove, preventing that excess material from reaching the first chamber. Accordingly, only a quantitively metered amount of specimen matter is allowed into the first chamber. The first chamber contains the metered volume of preserving fluid 25, preferably a liquid which will remain in contact with the specimen matter throughout storage and transportation of the vessel until part or all of it is drained for analysis by breaking the nib 5.

It should be noted that the preserving liquid in the first chamber could be safely secured initially by a breakable barrier across the aperture 20 of the septum or by a resiliently self-sealing aperture. In which case, at the factory, the stopper would be only partially engaged into the vessel, keeping the sample-holding portion into the second chamber. Only after collection of the specimen would the stopper be completely screwed into the vessel and the sample-holding portion forced through the septum. Instead of the end section 24, the first end of the vessel could be closed by a diaphragm through which a self-sealing access port can be practiced by means of a syringe or any other equivalent releasable sealing structure.

Figure 2:
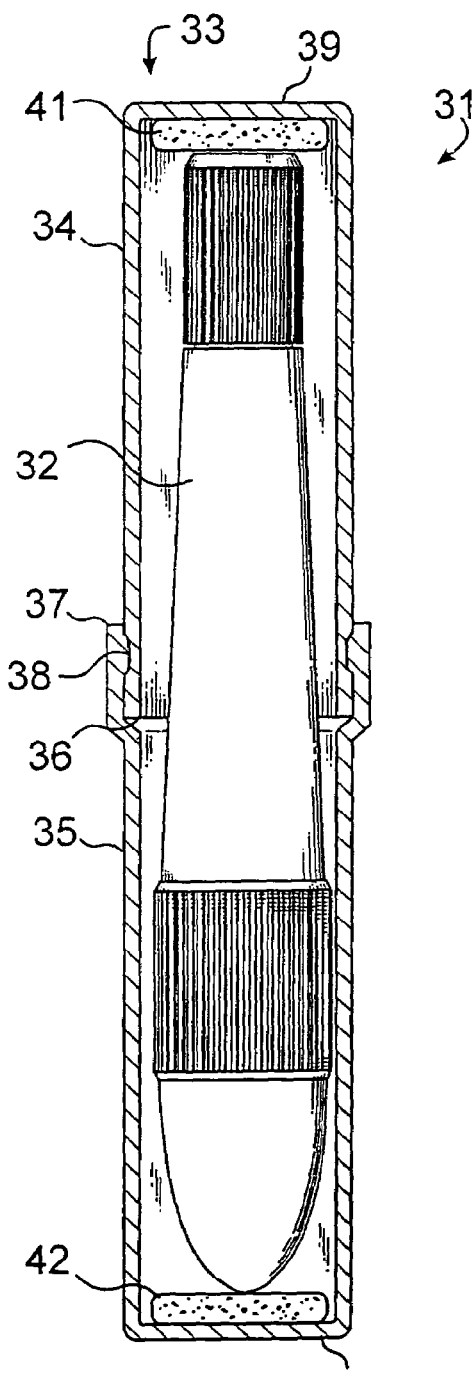

Referring now to FIG. 2, there is shown an alternate embodiment of a device 31 for collecting, storing and protectively transporting fecal or other similar biological matter. The device formed sililarly to the previous embodiment has a generally cylindrical vessel 32 having a gently tapering diameter. The entire vessel is loadable into a sealable shipping capsule 33 which comprises a pair of open-ended cups 34, 35 matable at the open ends 36, 37 along an annular snap connector 38. Each cup has a closed end 39, 40 having cushiion pad 41, 42 formed onto the inner surface. The capsule is preferably made from an inexpensive, durable, fluid-resistant material such as polyethanol plastic.

While the preferred embodiments of the invention have been described, modifications can be made and other embodiments may be devised without departing from the spirit of the invention and the scope of the appended claims.

What is claimed is:

1. A device, for quantitively collecting, preserving and mailing a specimen of fecal or other biological matter for later analysis, which comprises:
   a tubular vessel having a first closed end defining at least one sealed access port, a second open end opposite said first end;
   wherein said sealed access port comprises an end-breakable hollow nib, adapted to purposefully open said sealed access port upon breaking;
   a stopper shaped and dimensioned to close said open end; and
   a cover releasably occluding said sealed access port.

2. The device of claim 1, which further comprises a transversal septum in a median portion of said vessel, said septum dividing said vessel into a first chamber sealed by said closed end and a second chamber accessible through said second end, said septum further having an axial passageway therethrough defining a given cross-sectional geometry.

3. The device of claim 2, which further comprises a stick projecting from said stopper, said stick comprising a section being shaped and dimensioned to seal said passageway.

4. The device of claim 1, wherein the open end of said vessel and said stopper have cooperating screw threads.

5. The device of claim 1, wherein said cover is shaped and dimensioned to cap said closed end and nib.

6. The device of claim 2, which further comprises a liquid in said first chamber.

7. The device of claim 2, wherein said first chamber is doubly sealed at opposite ends.

8. The device of claim 7, which further comprises a stick projecting axially from said stopper into said vessel extending through and sealing said passageway.

9. The device of claim 8, wherein said stick comprises a sample-holding distal portion.

10. The device of claim 1, which further comprises an outer mailing capsule sized and shaped to fully enclose said vessel, stopper, and cover.

11. The device of claim 10, wherein said capsule comprises a matable pair of open-ended cylindrical cups, wherein each of said cups comprises a closed end.

12. The device of claim 11, which further comprises a resilient pad mounted upon an inner surface of said closed end.

* * * * *